US006623965B1

(12) United States Patent
Eberwine et al.

(10) Patent No.: US 6,623,965 B1
(45) Date of Patent: Sep. 23, 2003

(54) SIMPLIFIED USE OF 5' ENDS OF RNAS FOR CLONING AND CDNA LIBRARY CONSTRUCTION

(75) Inventors: James H. Eberwine, Philadelphia, PA (US); Roger Madison, Chapel Hill, NC (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/194,513

(22) PCT Filed: Apr. 25, 1997

(86) PCT No.: PCT/US97/06957

§ 371 (c)(1),
(2), (4) Date: Nov. 25, 1998

(87) PCT Pub. No.: WO97/41249

PCT Pub. Date: Nov. 6, 1997

Related U.S. Application Data

(60) Provisional application No. 60/016,617, filed on May 1, 1996.

(51) Int. Cl.[7] ........................... C12Q 1/68; C12P 19/34; C12N 15/64; C12N 15/63; C07H 21/04

(52) U.S. Cl. ........................ 435/455; 435/6; 435/91.2; 435/91.4; 435/91.41; 435/91.5; 435/320.1; 536/24.33; 935/18; 935/23

(58) Field of Search ..................... 435/6, 91.2, 91.4, 435/91.41, 91.5, 320.1; 536/24.33; 935/18, 23

(56) References Cited

U.S. PATENT DOCUMENTS 6,114,149 A * 9/2000 Fry et al. .................. 435/91.2

OTHER PUBLICATIONS

Meissner, P.S., "Bacteriophase λ cloning system for the construction of directional cDNA libraries", Proc. Nat'l. Acad. SCi. USA 84; 4171–4175 1987.

Okayama, H., "High–Efficiency Cloning of Full–Length cDNA", Mol. Cell. Biol. Feb. 1982 2;2 161–170.

* cited by examiner

*Primary Examiner*—Ethan Whisenant
*Assistant Examiner*—Joyce Tung
(74) *Attorney, Agent, or Firm*—Licata & Tyrrell P.C.

(57) ABSTRACT

A method of directional cloning using the 5' ends of RNAs for use, for example, in cloning and cDNA library construction is provided.

1 Claim, 6 Drawing Sheets

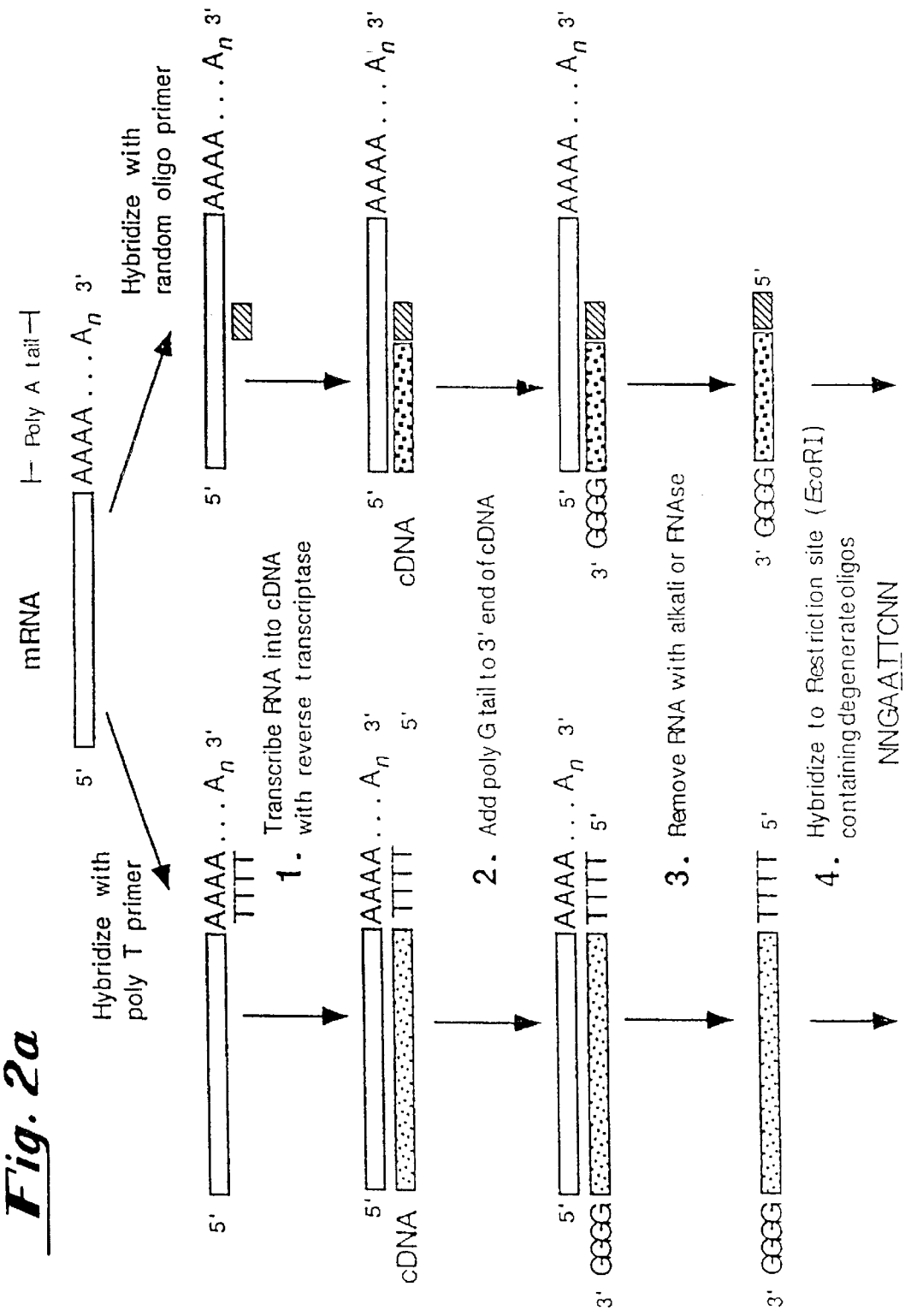

SIMPLIFIED USE OF 5' ENDS OF RNAS FOR CLONING AND CDNA LIBRARY CONSTRUCTION

This application claims the benefit of provisional application Ser. No. 60/016,617, filed May 1, 1996.

BACKGROUND OF THE INVENTION

Cloning of DNA sequences encoding expressed proteins and construction of cDNA libraries from poly A+ mRNAs isolated form cells and tissues is currently performed in accordance with procedures outlined in FIG. 1. However, the overall process is very laborious and has several technical limitations. Decreasing activity of the reverse transcriptase enzyme during first strand synthesis of the reverse complementary DNA (−) strand from the mRNA can result in yield of a product that is not full length. In addition, truncations can occur during the second round of synthesis to regenerate the corresponding "sense" coding (+) DNA sequences from the (−) DNA strand. For abundant mRNAs, a complete full length second strand is not always required as there is a greater likelihood for overlapping cDNAs that span a complete coding region. However, for smaller quantities of mRNA a full length strand may be only represented a few times.

As outlined in FIG. 1, the current procedure also requires homopolymeric tailing of both the cDNA sequences and the restriction digested cloning vectors, thus doubling the amount of manipulation involved. In addition, homopolymeric tailing of the vector results in loss of the original restriction site thereby limiting the ease of subsequent excision of the cloned cDNA region for the transfer to other expression or amplification vectors.

Accordingly, improvements to simplify cloning of mRNA sequences for use in the cloning of cDNAs for expression of proteins and in the construction of cDNA libraries are desired.

SUMMARY OF THE INVENTION

In the present invention a simplified method of directional cloning is provided. This method can be used, for example, in the cloning of the 5' ends of cDNAs. The present invention differs from prior art cloning methods requiring homopolymeric tailing of both cDNA sequences and restriction enzyme digested vectors along with complete second strand synthesis before homopolymeric tailing. The method of the present invention improves the efficiency of the cloning of 5' cDNA ends thereby increasing the likelihood of constructing full-length cDNA libraries comprised of overlapping cDNA subsequences.

The present invention uses oligonucleotides encoding restriction sites to create local double-stranded regions upon the first strand cDNA product of reverse transcriptase. The double-stranded regions are cleaved by double-strand requiring restriction endonucleases and serve to limit the regions to be replicated in a second (+) strand synthesis. Use of these oligonucleotides also increases the accuracy of replication of the entire shorter (−) cDNA strand to yield more of the 5' (+) cDNA sequences necessary for obtaining a full representation of the entire mRNA coding sequence.

The method of the present invention also uses an oligonucleotide primer containing the same restriction site that is homopolymerically tailed to complement the homopolymerically tailed 3' end of the (−) cDNA strand. The 5' end of this primer hybridizes to the palindromic complement 3' end of the restriction digested (−) cDNA strand thereby forming a more stable and replication competent gapped single-stranded circle. The resultant double-stranded product contains a unique copy of the targeting restriction site encoded by the priming oligonucleotide. Cleavage at this site yields double-stranded cDNA containing pairs that can be directly ligated into appropriate multiple cloning sites of commercial cloning and expression vectors. Since the restriction site is preserved and flanks the cDNA insert, the desired cDNA sequences can be readily excised and transferred to other vectors if necessary.

DETAILED DESCRIPTION OF THE INVENTION

Figure 1:
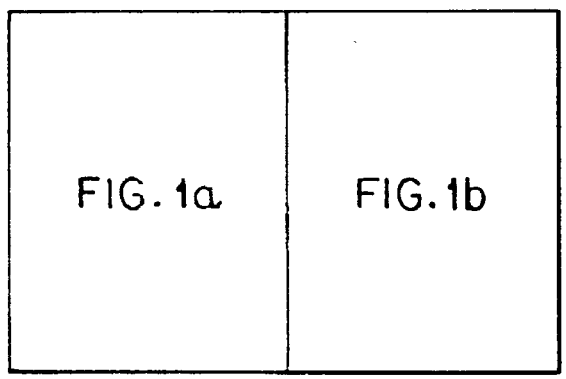
FIG. 1 is a schematic detailing the steps required by prior art procedures used to obtain cDNA clones from poly A+ mRNA. A complete set of clones containing different cDNAs representing all possible coding sequences derived from isolated mRNAs constitute a cDNA library. Regions of RNA, first strand (−) DNA and second strand (+) DNA are indicated by different stippling patterns in the bars. The nucleotide sequences of homopolymeric tailings are indicated in bold type. Steps are numbered sequentially as indicated. Those listed on the left are for preparation of cDNA. Those listed on the right are for preparation of the cloning vector.
Figure 2:
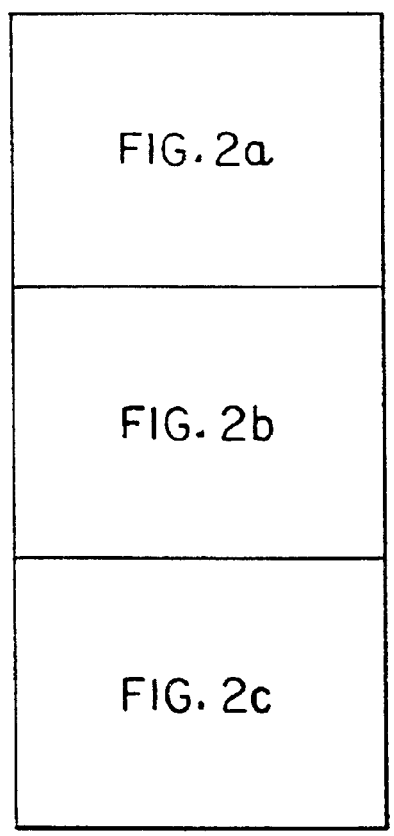
FIG. 2 is a schematic detailing the steps of the method of the present invention when used for obtaining cDNA clones. The left portion of the figure show the method for cDNAs derived from oligo-dT priming. The right portion of the figure shows the method for random priming of the poly A+ mRNA.
Figure 1A:
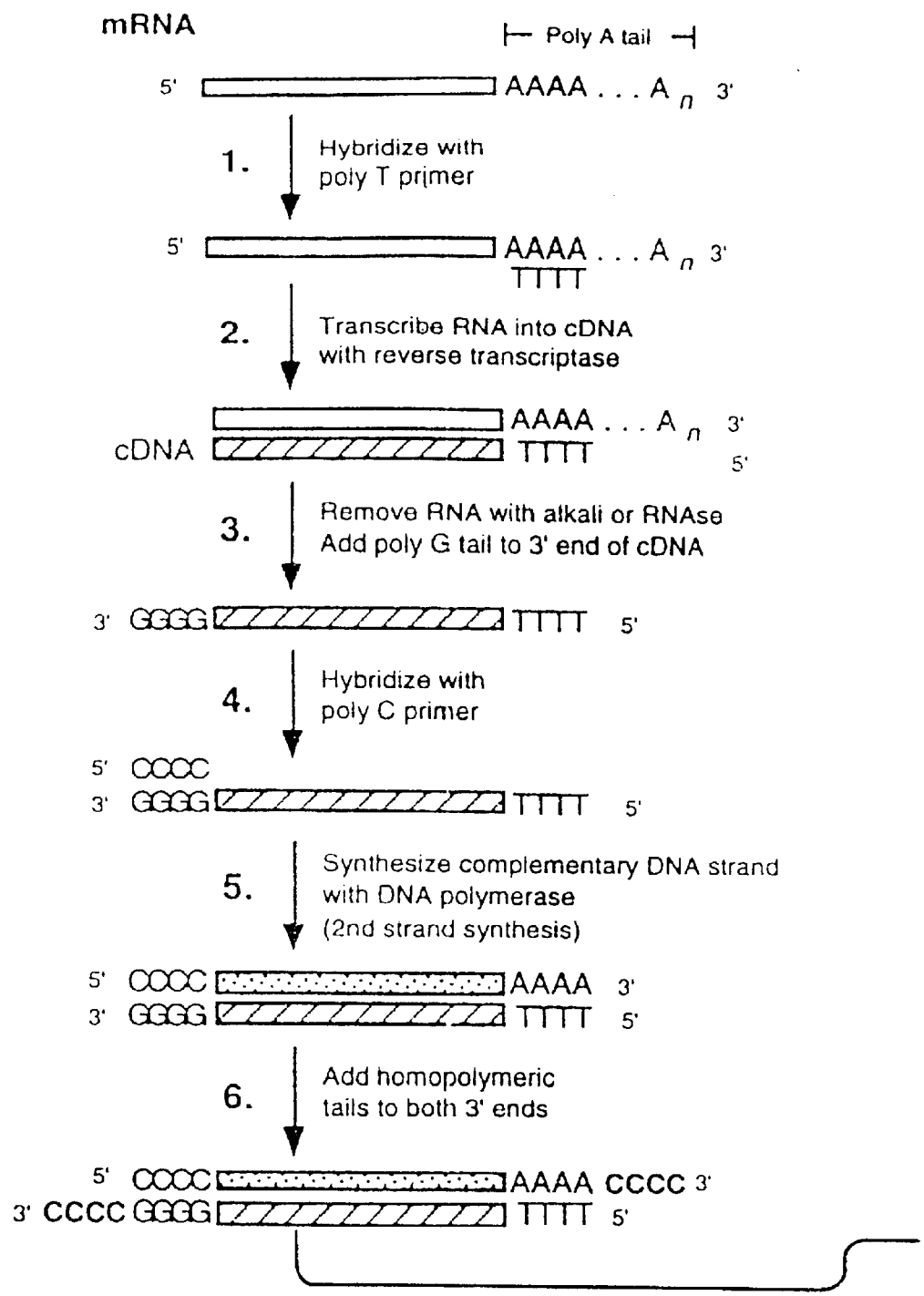
Figure 1B:
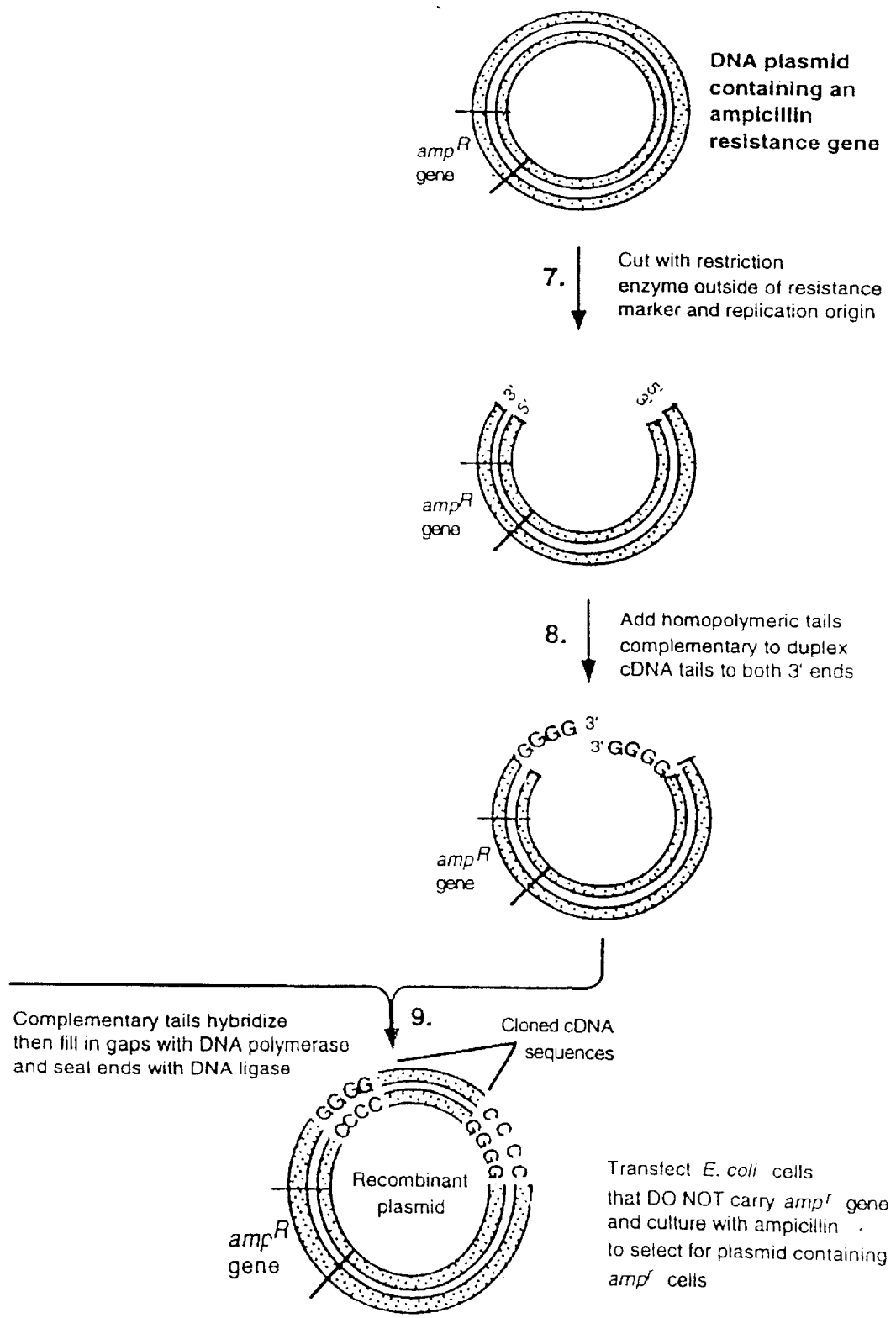
Figure 2B:
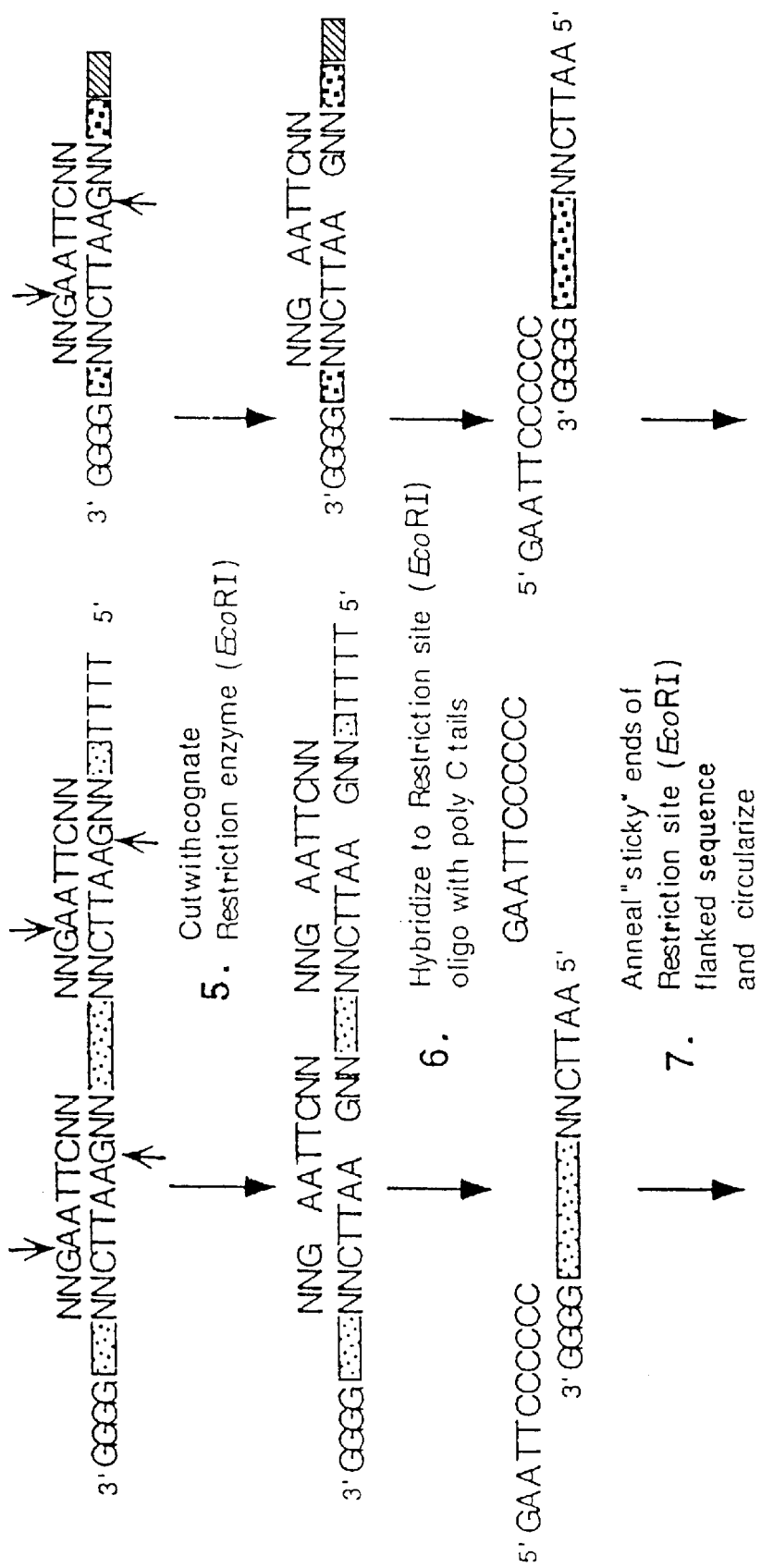
Figure 2C:
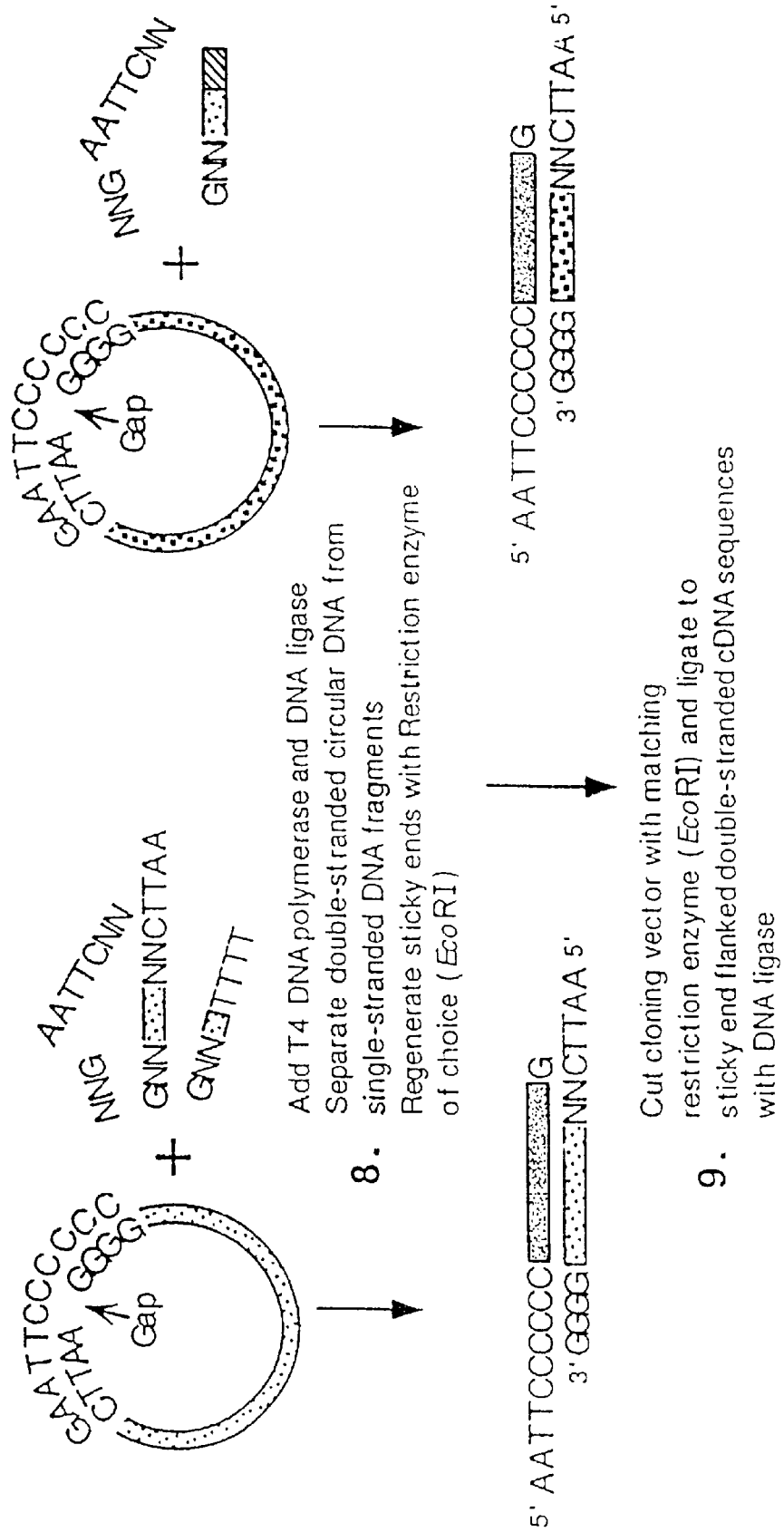

The present invention provides a method of directional cloning which uses the 5' ends of RNAs, for example, to obtain cDNA clones. A detailed schematic of the method of the present invention being used to produce cDNA clones is provided in FIG. 2. In this embodiment, oligo-dT or random priming of poly A+ mRNA is used to generate (−) first strand cDNAs. These cDNAs are then homopolymerically tailed with dG or dC using terminal deoxynucleotidyl transferase. After tailing, the heteroduplex is denatured by heat and the mRNA removed by alkaline hydrolysis or RNAse digestion to yield single-stranded (−) cDNA. The single-stranded (−) cDNA is the mixed with an first oligonucleotide incorporating a palindromic restriction site in the middle which is flanked on both the 5' and 3' sides with at least two completely degenerate nucleotides. In a preferred embodiment the first oligonucleotide consists of ten bases, including a 6 base palindromic restriction site, such as that for EcoRI, flanked by two degenerative nucleotides, as the ten base overall length allows a high degree of specificity of targeting with reasonable annealing temperature. However, this oligonucleotide can be longer to incorporate other palindromic restriction endonuclease recognition sequences. Examples of restriction endonuclease recognition sequences which can be used include, but are not limited to, BglII, ClaI, EcoRV, SacI, KpnI, SmaI, BamHI, XbaI, SalI, AccI, AvaI, PstI, SphI, HindIII, HincII, NsiI, NotI, SfiI, ApaI, NcoI, StuI, NdeI, PvuII, and XhoI. After mixing, the oligonucleotide-cDNA mixture is slowly cooled from 50° C. to 37° C. and the cognate restriction enzyme is added. The resulting annealed, short double-stranded DNA segments correspond to the positions of these restriction sites on the (−) cDNA. Cleavage by the cognate restriction enzyme yields single-stranded cDNAs bound on their 5' end by the "sticky end"

left by the restriction enzyme used and on their 3' end by a poly-dG or -dC tract. Thus, the method of the present invention allows specific site-directed cleavage of the single-stranded (−) cDNA thereby eliminating the need for second strand synthesis of the entire (+) cDNA to provide the double-stranded restriction site as in prior art methods. Accordingly, the present invention is much simpler and requires less time than the prior art methods. Further, considerably smaller amounts of oligonucleotide triphosphate reagents are required.

A second oligonucleotide comprising nucleotides complementary to the 3' end of the cDNAs and containing the same restriction site as in the first oligonucleotide is then annealed to the 3' poly-dG or -dC tailed single-stranded (−) cDNA by a similar cycle of heating and slow cooling as described above. Since this single-stranded (−) cDNA contains the cognate "sticky end" at its 5' terminus, the 5' end can loop back and also anneal to the second oligonucleotide at the restriction site. The resulting primed and gapped single-stranded (−) cDNA is stabilized and rendered replication-competent for second strand synthesis of (+) cDNA by the addition of a DNA polymerase and DNA ligase. Since the cDNA region to be replicated is shorter than the original full-length sequence, the likelihood of it being completely and accurately replicated is increases over standard methods requiring the traverse of a longer region of (−) cDNA. The resulting double-stranded closed-circular cDNA is readily separated from linear single-stranded fragments and trinucleotides by spin column chromatography or agarose gel electrophoresis.

In addition, the resultant double-stranded cDNAs are readily linearized with the cognate restriction enzymes to regenerate "sticky ends": compatible for direct ligation into vectors similarly linearized. This eliminates the extra effort in homopolymeric tailing of the vector prior to insertion of the cDNA by prior art methods. Further, the method of present invention preserves the cloning restriction site thus allowing ready excision of the desired cDNA sequences by the same restriction enzyme.

As will be obvious to those of skill in the art upon reading this disclosure, the directional cloning method of the present can also be used in different embodiments. For example, by utilizing a complete set of oligonucleotides containing the common restriction sites utilized in the multiple cloning sites of plasmid or phage vectors, the present method can be used to provide a complete set of restriction site delimited cDNA sublibraries which would greatly facilitate both cloning and sequence analysis of cDNAs. A mRNA can be effectively scanned for all potential restriction sites thereby ensuring that a cDNA sublibrary would encode the corresponding desired 5' ends for almost all encoded mRNA.

What is claimed:

1. A method of cloning DNA comprising:

(a) priming poly A+ mRNA to generate (−) first strand cDNAs;

(b) homopolymerically tailing the (−) first strand to form a heteroduplex;

(c) denaturing the heteroduplex;

(d) removing the mRNA to yield a single-stranded (−) cDNA;

(e) mixing the single-stranded (−) cDNA with a first oligonucleotide, said oligonucleotide comprising a restriction site, to produce annealed, short, double-stranded DNA segments corresponding to positions of the restrictions site on the single-stranded (−) cDNA;

(f) cleaving the double-stranded DNA with a restriction enzyme specific to the restriction sites to yield single-strand cDNAs bound on their 5' end by a sticky end left by the restriction enzyme and on their 3' end by a poly-dG or poly-dC tract;

(g) annealing a second oligonucleotide comprising nucleotides complementary to the 3' end of the single-stranded cDNAs and containing the same restriction site as in the first oligonucleotide to the 3' end of the single-stranded cDNA so that the 5' end of the single-stranded cDNAs can loop back and also anneal to the second oligonucleotide at the restriction site to form primed and gapped single-stranded (−) cDNAs; and (h) adding DNA polymerase and DNA ligase to the primed and gapped single-stranded (−) cDNAs.

\* \* \* \* \*